United States Patent [19]

Casnig

[11] Patent Number: 5,134,070
[45] Date of Patent: Jul. 28, 1992

[54] METHOD AND DEVICE FOR CELL CULTIVATION ON ELECTRODES

[76] Inventor: Dael R. Casnig, 234-324 Cambridge St. North, Ottawa, Ontario, Canada, K1R 7B3

[21] Appl. No.: 605,392

[22] Filed: Oct. 30, 1990

Related U.S. Application Data

[60] Division of Ser. No. 532,651, Jun. 4, 1990, which is a continuation-in-part of Ser. No. 489,976, Mar. 7, 1990.

[51] Int. Cl.⁵ .................. C12N 13/00; B01D 57/02; B01D 61/42
[52] U.S. Cl. .................. 435/173; 435/284; 435/287; 435/297; 435/289; 435/310; 435/817; 204/180.1; 204/406; 204/299 R; 935/85; 935/52; 935/93
[58] Field of Search ............... 204/180.1, 406, 299 R, 204/15; 435/173, 284, 289, 297, 310, 817, 287; 935/85, 52, 93

[56] References Cited

U.S. PATENT DOCUMENTS

| | | | |
|---|---|---|---|
| 4,699,881 | 10/1987 | Matschke | 435/287 |
| 4,804,450 | 2/1989 | Mochizuki et al. | 435/173 |
| 4,818,697 | 4/1989 | Liboff et al. | 435/173 |
| 4,923,814 | 5/1990 | Marshall | 435/173 |

OTHER PUBLICATIONS

Yaoita, et al., Exp. Cell. Biol., 57(1), pp. 43-51 (1989).

*Primary Examiner*—David L. Lacey
*Assistant Examiner*—William Chan

[57] ABSTRACT

A method and device are disclosed for culturing of adherent cell monolayer cultures on an electrode surface and subjecting the cells to an electrical field. The device may generally comprises cell culture dish, for example a petri-type dish, having a bottom, with an electrically conductive, optically transparent coating amenable to cell adhesion on the upper surface of the bottom. A metal electrode may contact the underside of the coating and is connected to a source of electrical power. The method involves use of the device for culturing the cells under the intermittent or continuous influence of an electric field, or during the establishment of an electrical field or potential. Further, a method and device are disclosed for the sensing of cell poration, and the use of this information to automate the process of electroporation. Further yet, a device and method are disclosed for use in assisting in the time-correlated mapping of the sequence of serial and parallel gene replication.

22 Claims, 9 Drawing Sheets

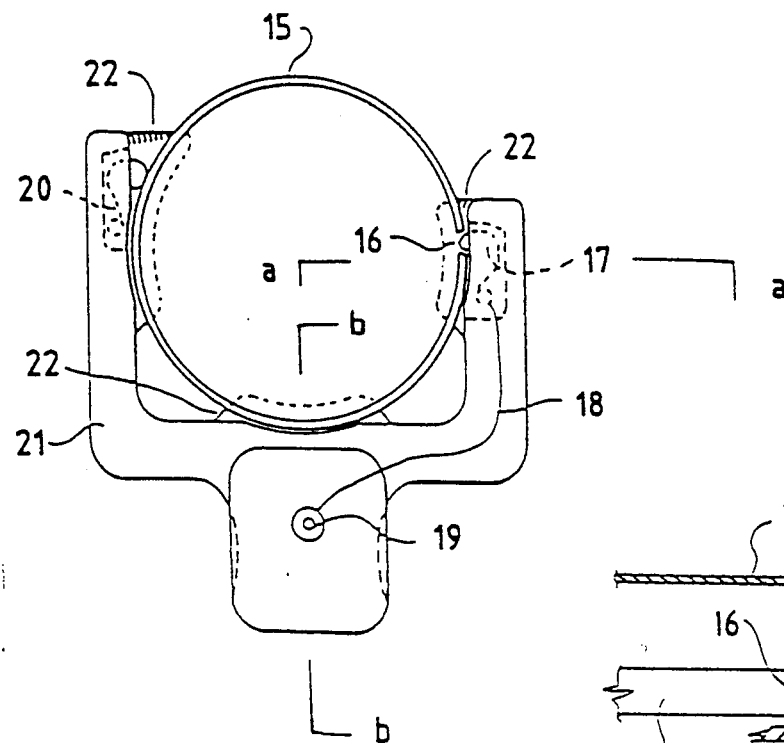
FIG. 8
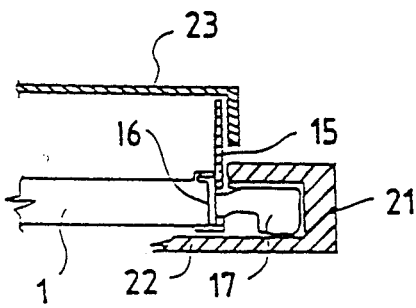
FIG. 8a
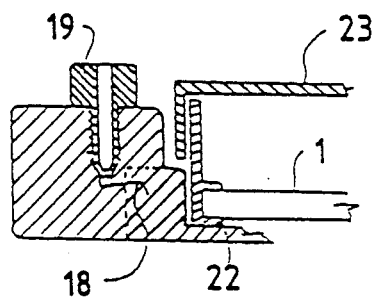
FIG. 8b
FIG. 9
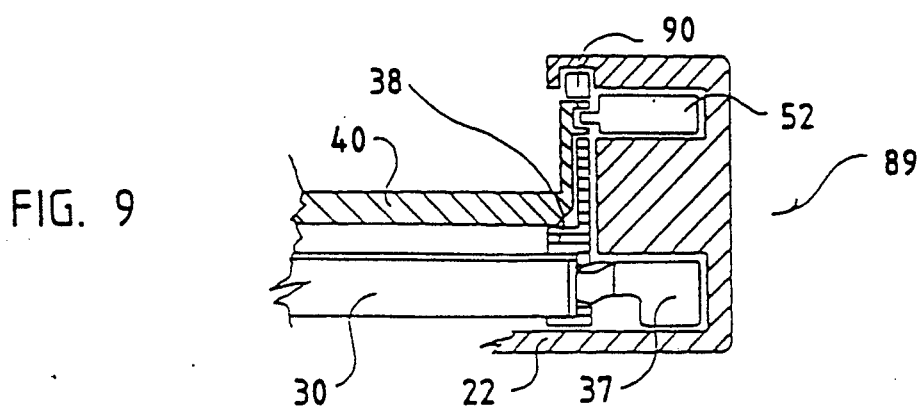

METHOD AND DEVICE FOR CELL CULTIVATION ON ELECTRODES

CROSS REFERENCE TO RELATED APPLICATION

This application is a divisional of U.S. application Ser. No. 632651 filed June 4 1990, which is a continuation-in-part of my application Ser. No. 489,976 filed Mar. 7, 1990.

BACKGROUND OF THE INVENTION

The present invention relates generally to devices and methods for the culturing of cells on electrode surfaces, and more specifically to culture dishes for the culturing of adherent normal cell monolayer cultures wherein they may be subjected to an electric field or discharge and to the use of transparent thin film electrodes conducive to cell adhesion for use in conjunction with such applications.

The term "petri dish" as used herein refers to that "shape/function", familiarly known to those skilled in the art of cell culture as a petri dish. The term "pepetri dish" is used herein to refer to a planar electrode petri-type dish according to one embodiment of the invention. The terms "fluid", "media" and "medium" as used herein refer to such materials as may be used for the culturing and or suspension of cell cultures. Similarly, the terms "electroporation fluid" or "electroporation medium" refer to those groups of materials and solutions that may be used in the process of electroporation.

The expressions "cell/s", "culture/s", and "cell culture/s" as used herein include those operations starting from the process of "plating", and up to and including the stage known as "confluency"; i.e. from a starting point of one cell to the point at which the culture surface is entirely covered by a monolayer of cells and substantially no further cell division occurs in normal cells. This range is meant to include known cell culturing techniques, such as synchronous culturing, and those that make up the wide range that would be used in micro-biology, neuro-biology, pharmacology and other related fields of endeavour.

The term "exogenous materials" as used herein refers to macromolecules such as DNA, RNA, proteins, plasmids, and other such materials that may be of interest for introduction into a living cell.

Adherent cells/cultures as used herein refers to those types of cells that are anchorage-dependent for growth.

Diverse biological responses to electric fields, both applied and endogenous, continue to motivate experimental searches for mechanisms of electromagnetic interactions with cells. Jaffe, L. F. (1979) Control of development by ionic currents. In Membrane Transduction Mechanisms. R. A. Cone and J. E. Downing editors. Raven, N.Y. 199-231, has shown that cell development is effected by an electric field, while Borgens, R. B., J. W. Vanable, Jnr., and L. F. Jaffe (1977) Bioelectricity and Regeneration. I. Initiation of frog limb, describe the effect of electric fields on cell regeneration. Many other basic cellular functions, including motility and receptor regulation are also modulated by applied external electric fields. In addition, cell membrane permeabilization and fusion have been effected by applied fields (see Zimmerman, U., and J. Vienken (1982) Electric field-induced cell-to-cell fusion. J. Membr. Biol. 67:165-182; Tessie, J., V. P. Knutson, T. Y. Tsong, and M. D. Lane (1982) Electric pulse-induced fusion of 3t3 cells in monolayer culture. Science (Wash. D.C.). 216:537-538; and Potter, H., L. Wier, and P. Leder (1984) Enhancer-dependent expression of human K immunoglobulin genes introduced into mouse pre-B lymphocytes by electroporation).

Local perturbation of plasma membrane potentials provides a hypothetical mechanism for the interaction of applied electric fields with cells.

Thus, Canadian Patent No. 1,208,146 (Wong) describes a method of transferring genes into cells which comprises subjecting a mixture of the genes and the cells suspended in a liquid medium, and subjected to an electric field and electric discharge. U.S. Pat. No. 4,663,292 (Wong) discloses a method of transferring genes into cells and fusing cells, which comprises subjecting suspensions of genes and cells and cells to an electric discharge.

U.S. Pat. No. 4,695,547 (Hilliard et al) relates to a multi-welled tray that contains a suspension of cells and the foreign molecule, and wherein a ring-shaped metallic electrode configuration that does not interfere with visual observation by inverted microscope during the procedure is received from above within the well. U.S. Pat. 4,764,473 (Matschke et al) discloses a device for the electroporation and electrofusion of cells using a double helical metallic electrode configuration and is for the application of electric fields to cells in suspension.

U.S. Pat. No. 4,561,961 (Hofmann, see FIG. 3,) discloses an electrofusion apparatus wherein a sandwiched chamber containing the metallic electrodes may be placed in the microscope, while German Offen. 3,321,239 (Zimmermann et al) describes an electrofusion cell of very simple structure.

A large percentage of interest in mammalian cell lines lies in the group known as adhesion-dependent types. Most primary fibroblasts proliferate when attached to glass or plastic, but do not grow while in suspension. Adhesion dependent cells do not adhere to metallic surfaces. Studies into "anchorage dependance", a term that describes the inability of normal cells to grow unless attached to a substratum, have shown that cells do not enter the S-phase (i.e. the reproduction cycle of cell growth when DNA is undergoing replication) unless attached to an appropriate substratum. While significant work has been done towards understanding the interaction between cells and applied electric fields, this has been virtually restricted to single cells in suspension, and is therefore of very limited application in the study of the far more complex interplay between applied electric fields and cells in monolayer culture tissue, and virtually no work has been able to be done on cells while in the S-phase of growth.

Certain procedures such as electroporation and electrofusion require subjecting cell samples to electric fields. Treating the cells entails trypsinizing the cells, rinsing, suspending them in an appropriate fluid carrying the foreign molecule, in most cases chilling the resulting suspension, subjecting the cells to the electric field, rinsing, and then re-plating them.

Current cell electroporation equipment requires the significant expenditure of relatively high voltage and current, to the point that cooling is often a concern. This is due to the relative inefficiencies in mutually dependent system parameters, such as the number of cells per unit volume of electrolytic media; the conductivity and composition of the electrolytic media; the voltage being applied; the time period of pulse, the location of the cell relative to the electrode; and the area of membrane surface being presented in relation to the electrodes (spherical) are all factors which require attention when using suspensions and does not account for any change incurred in the cell or to the membrane as a result of being put into suspension. The exogenous material (DNA/RNA code, etc.) that it would be of interest to have expressed as a measurable cell function upon successful integration is open to cyto-enzymatic attack until integrated or metabolized. Normal cell function is recovered after when the electrical inducing poration is no longer present, but progression of normal cell functions such as replication can not occur until sufficient adhesion is regained to induce a growth signal. A significant period of time may elapse between the poration process and potential integration and has an affect on efficiency. Depending upon the cell condition after transmembrane inductance of exogenous material and the type of material introduced, transient, stable or no expression may be expected. Due to the adverse conditions imposed in the process to date, a large percentage of cells die, some give a transient expression and fewer still exhibit a permanent stable expression.

Because of this large number of cell deaths, a shift in the base population occurs since a first level of selection (survivors vs non-survivors) has been made which further complicates matters.

It is the purpose of this invention to overcome many of the above stated drawbacks as currently known in the art and to significantly advance the state of the art.

SUMMARY OF THE INVENTION

The object of the present invention is to provide means and methods wherein monolayer adherent cells may be cultured on electrode surfaces.

It is another object of the present invention to provide a structure and method for the growth and study of monolayer adherent cell cultures on while on electrode surfaces and while being subjected to electric fields, the object being that changes that occur during the various stages of the life cycle of a cell, and especially of those that occur the S-phase of a cell's life; the effects of applied electrical fields upon growing cells; and cell interactions with contact electrode surfaces, may all be studied optically with the growth surface either electrically neutral or in an electrically ionized state.

It is another object of the invention to allow an in vitro culture of cells to be equally affected by an electrical discharge.

It is another object of the present invention to be able to automatically determine the required intensity of electrical discharge to induce poration.

It is another object of the invention to be able to subject the cells to an electric discharge intense enough to induce poration, and not cause damage to the cells by heat or other secondary effects.

Accordingly, one aspect of the invention provides cell culturing devices, which comprise: substrates, electrically conductive coatings conducive to cell adhesion and growth thereon, and electrode means in contact with said coatings for applying an electric potentials or electrical ionizing sources to said coatings to establish an electrical field above said coated substrates.

A further aspect of the invention provides culture devices, which comprise transparent substrates, electrically conductive, optically transparent coatings conducive to cell adhesion and growth thereon, and electrode means in contact with the coatings for applying electric potentials or electrical ionizing sources to the coatings to establish an electrical field above the coated substrates.

A further aspect of the invention provides an electro-culturing petri dish, comprising a transparent planar substrate, an electrically conductive, optically transparent coating conducive to cell adhesion and growth thereon, and electrode means in contact with the coating for applying an electric potential or electrical ionizing source to the coating to establish an electrical field above the coated substrate. A further aspect of the invention provides an electrode, which may be transparent, disposed above the cell culture creating an electrode chamber wherein the cells may be subjected to an electrical discharge.

A further aspect provides detector electrodes disposed on the opposed electrodes in the chamber so as to be able to detect the real-time effect of the electrical discharge on the cells and the electrode chamber fluid.

A yet further embodiment provides microprocessor means to control the time and intensity of electric discharge so as to induce poration and uses the detection of the poration to terminate the process.

Hitherto, a restriction to researchers in the area of applying electrical fields to cells, and to adherent monolayer cells in particular, has been the fact that experiments involving adherent cells and electric fields have been essentially constrained to non-replicative phases in cell's lives because cells are usually treated while in suspension. Those devices that may be used while the cells are not in suspension, suffer from the fact that the lines of force generated by an electric field are propagated in a side-to-side fashion across the cells being grown.

Petri dishes have been in existence since before the turn of the century and the ability to create transparent conducting thin films was first noticed by Baedeker in 1907, but remained a scientific curiosity until the Second World War, when they were used to deice aircraft windows. A wide variety of materials may be used for the thin film and a wide variety of techniques used to apply them, such as are disclosed in Jarzebski, Z. M., Preparation and Physical Properties of Transparent Conducting Oxide Films, Institute of Solid State Physics, Zabrze, Poland (1982); Vossen, J. L., Transparent Conducting Films, RCA Corporation David Sarnoff Research Center, Princeton, N.J.; and Haacke, G., Transparent Conducting Coatings, Ann. Rev. Mater. Sci., 1977.7:73–93.

As indicated above, one aspect of the invention contemplates the application onto the upper surface and side of a substrate which forms the transparent floor of a dish, of a layer of optically transparent, electrically conductive material that is amenable to cell adhesion. The substrate is optically, chemically and electrically neutral, and may be formed, for instance, of glass or certain plastics. The applied surface coating may be circumferentially attached to an annular wire, thin-film layer of a metal deposited between the substrate and the coating, or strip of metal which passes through a wall of the tubular enclosure forming the walls of the dish, so as to provide an electrical connection at the outer face of the wall.

The coating itself may be varied in application such that a number of differing iso-electric potentials may be created, such as with a flat thin film in cross-section, or, a layer that is thin at the annular outside, and increases in depth at a controlled rate to the center of the dish, such that a relatively uniform iso-electric potential may be manifested over the entire surface of the floor of the dish. An alterant method is to dispose a layer of a thin-film conductor, which may be transparent, having greater conductivity that the cell adherent coating, between the coating and substrate.

Another aspect of the invention provides a method of culturing cells on electrode surfaces, which comprises culturing the cells on a substrate coated with an electrically conducting layer conducive to cell adhesion and growth, and subjecting such cells to an ionizing electric field or electrical potential while AD situ on the substrate during the monolayer adherent cell culturing by applying an electrical potential to the layer. If desired, this method may be carried out on a device comprised of a transparent substrate and transparent cell adherent electrode coating means so that one may optically study the cells, their behaviour, and their response to various intensities of electrical fields through the coated substrate during charging of, and while the coated substrate is charged.

Thus, the invention affords a method and means of subjecting monolayer adherent cells to a planar projected ionizing electric field or electric discharge while they are being cultivated, thereby removing the need to transfer the cells to an electrode chamber and thereby removing the disruption of their normalized growing phase with either chemical or mechanical methods, such as the application of a proteolytic enzyme or scraping off the cells from the culturing dish with a rubber policeman.

The electrical potential may be applied continuously or intermittently and may be as low as a few volts or as high as about 2000 V depending upon the desired range and may be constant or variable in nature. The electrical potential may be applied at least partially during the S-phase of a synchronized cultures, life for instance.

The device offers an exceptional and hitherto nonexisting means of subjecting adherent cell cultures to electric fields, but is not limited in use to only that type of cell culture. Cells to be cultured may be, for instance, eucaryotic, procaryotic, plant or mammalian cells.

It will be apparent to the skilled observer that systems hitherto available, do not allow, nor have they provided for the possibility of, subjecting monolayer adherent cell cultures to an applied electric field and to an applied planar-projected electric field while in situ, in the petri dish in which they have been cultured. This represents an important advantage of the system provided by the present invention over the prior art.

Other features, advantages, objects and embodiments of the invention will be readily apparent to those skilled in the art from the following description of a preferred embodiment taken in conjunction with the appended claims, and accompanying drawings.

DESCRIPTION OF THE DRAWINGS

FIG. 3a is a partial cross-section of the dish shown in FIG. 2a, taken along line III—III of FIG. 2a.

FIG. 5b shows an alternate embodiment of FIG. 2a;

FIG. 8 is a plan view of an embodiment of apparatus for use with the planar electrode cell cultivation dishes;

FIG. 8b is a cross-section of part of the apparatus of FIG. 8, taken along line B—B of FIG. 8;

FIG. 8c is a cross-section of part of the apparatus of FIG. 8, taken along line C—C of FIG. 8;

FIG. 9 shows a partial cross-section of a modification of FIG. 8b for use with the pepetri and a counter electrode.

DESCRIPTION OF THE PREFERRED EMBODIMENTS

Figure 1:
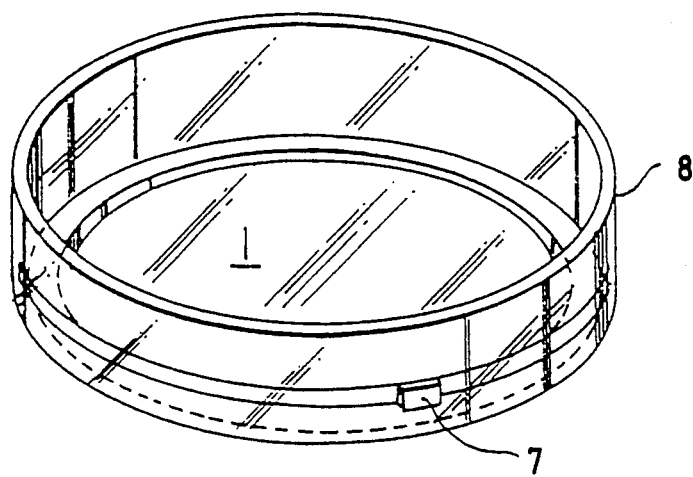
FIG. 1 is a perspective view, partly from above, of a planar electrode cell cultivation dish according to an embodiment of the present invention.

Referring now to FIGS. 1 to 3a, an electrode cell cultivation dish is shown which comprises a substrate 1 in the form of a circular disc of optically transparent glass, for example Corning's Pyrex* brand, or plastic, having polished edges, disposed in a tubular glass or plastic enclosure 6.

A conductive surface coating 2 conducive to cell adhesion, and for transparent electrodes preferably having a thickness of from 0.1 to 5 microns, and thicker where transparency is not required, is deposited over the upper surface and the edges of substrate 1, and extends over these surfaces as an uninterrupted coating. A distribution electrode 4 in the form of a thin annular metal strip encloses the edge of the substrate 1, on the outside of the surface coating 2. The distribution electrode 4 may be formed, for instance, of a conductive material such as copper, tin, platinum, silver or an alloy containing one or more thereof.

Positioned between the surface coating 2 and the distribution electrode 4, is a wettable metallic coating 3 that intimately contacts and wets both the outer surface of the surface coating 2 and the inner surface of the distribution electrode 4, so as to minimize the contact resistance to electrical flow which might otherwise occur as a result of surface or dimensional imperfections in either or both the substrate 1 and the distribution electrode 4. The metallic coating 3 may be formed of a conductive alloy which may be liquid at room temperature, for example a gallium indium alloy and particularly a GaIn 90:10 allow. Alternatively, the metallic coating 3, may be liquid at a significantly higher temperature so as to be solid at cultivation and autoclaving temperatures.

The distribution electrode 4 completely encircles the substrate 1, and overlaps upon itself a sufficient distance to allow bonding together of the two ends thereof. Attached to one point on the distribution electrode 4 and extending radially from the outer surface thereof is a lead-in wire 5 (see FIG. 3), for example a platinum or copper wire, that passes cleanly through one wall of the tubular enclosure 6, and terminates in contact with an outer electrical contact 7 disposed in or on the outer surface of the enclosure 6.

The outer electrical contact 7 is a metal strip, for example, formed of platinum, preferably mounted flush into the outer surface of tubular enclosure 6, so as to allow the external application of electricity to be propagated entirely around the outer circumference of the substrate 1 by means of the annular distribution electrode 4 and thence along the plane of the coating 2 on the upper surface of the substrate 1.

The tubular enclosure 6, circumferentially encloses the substrate 1, the surface coating 2, the metallic coating 3, and the distribution electrode 4. The enclosure 6 is provided with spaced annular flanges 6a and 6b which extend radially inward over the upper and lower surfaces of the substrate 1 a sufficient distance so as to preclude the leakage of fluid. The enclosure 6 also extends perpendicularly upwards from the plane of the upper surface of the substrate 1, i.e. in the manner of a tube, so as to create a well or chamber of sufficient depth to allow the cultivation of cells on the surface of the surface coating 2.

The exact method of deposition used to form the surface coating 2 will depend upon parameters such as the particular materials employed, the desired thickness of the coating, the substrate/coating interface shape, the availability of equipment, economic factors associated with each of the methods, etc. Some suitable techniques include R.F. sputtering, D.C. reactive sputtering, thermal evaporation, electron beam evaporation, dipping and curing. Those skilled in the art will be aware of other suitable methods or will be able to ascertain them using no more than routine experimentation. Those skilled in the art will also be aware of variations of the above techniques, such as electric field ion depletion of the substrate so as to enhance the conductivity of the coating.

Figure 2:
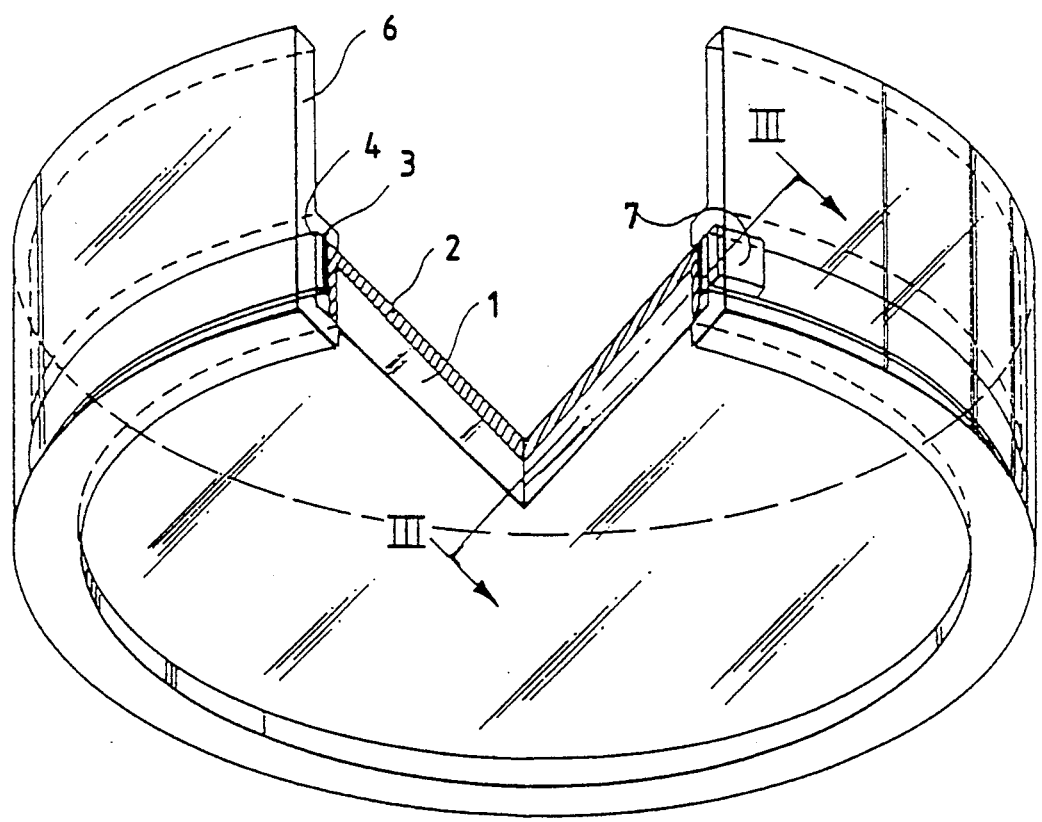
FIG. 2 is a cutaway isometric view of the dish of FIG. 1 on an enlarged scale, showing the interrelationship of the component parts of the dish.
Figure 2A:
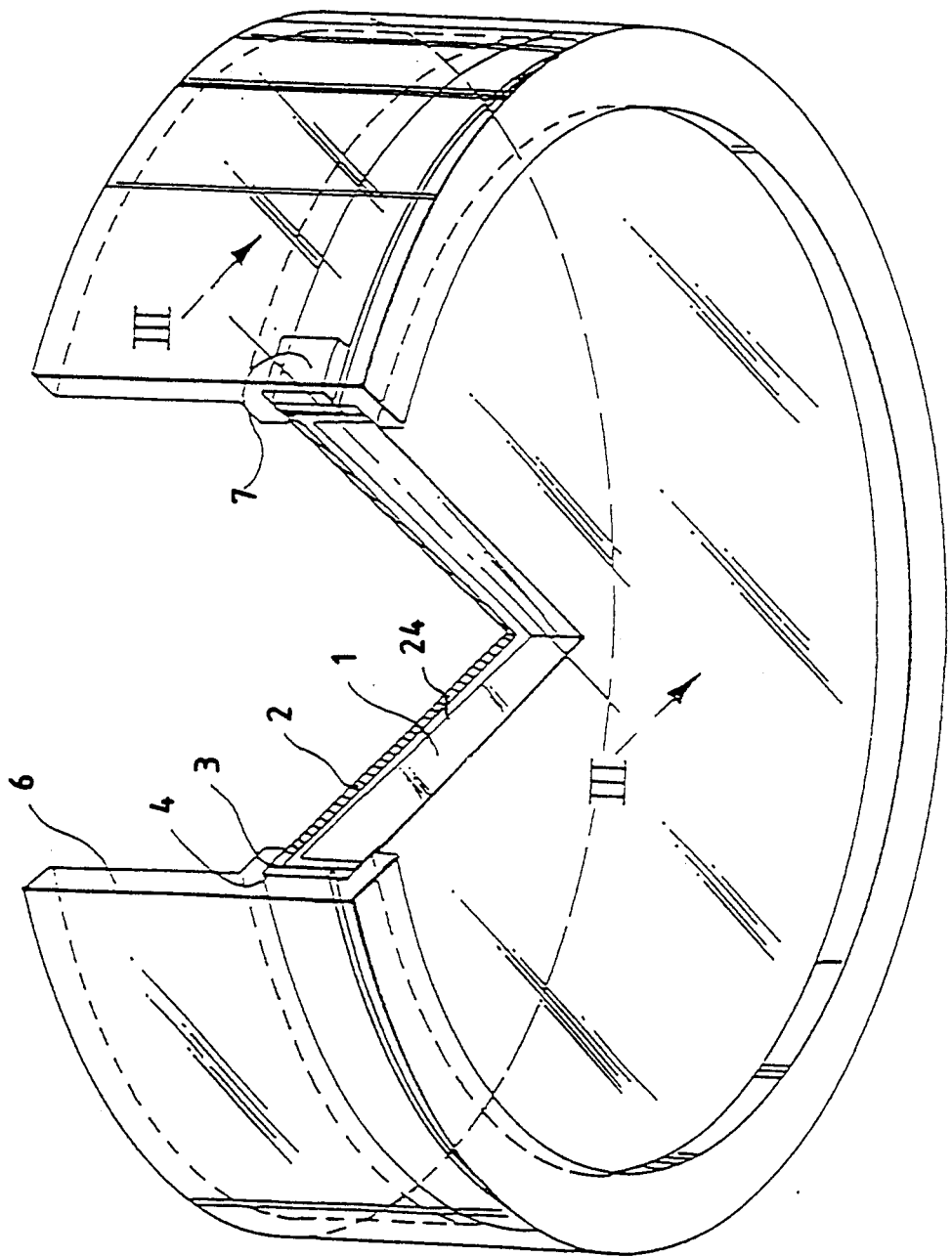
FIG. 2a is a cutaway isometric view of a dish of an alternate embodiment showing a distribution electrode layer formed under the coating of the instant invention.

Since conductive and semi-conductive thin films tend to suffer from high in the plane resistance, an alternate method is shown in FIG. 2a where there is deposited a transparent, thin film 24 of metal, preferentially one of the noble metal family, e.g. platinum or gold, of approximately 50 to 200, e.g. 100, Angstroms thickness onto the base substrate 1 forming a radial distribution electrode upon which a thin layer of coating 2 having a thickness of 0.1 to 5 microns of suitable material for cell adhesion, preferably of tin and/or indium oxides, is deposited. This arrangement gives rise to an overall reduction in resistance. In a further embodiment, the preferably noble metal may be replaced by a further semi-conductor having better conductivity properties, but unusable as a cell cultivation surface for reasons such as toxicity, electro-chemical stability, etc. This second semi-conductor would, as the noble metal film, have deposited on its' surface, semi-conductor materials conducive to cell growth such as tin oxide or pin oxide with indium, etc. If a transparent thin-film layer of metal, or a layer of a more conductive transparent thin-film semi-conductor is applied firstly to the substrate, the coating may be in the thinner range stated above.

In yet a further alternative embodiment, where transparency is not required, the conductive coating conducive to cell adhesion and growth may be directly applied onto a metal wherein the metal would serve as the means to reduce the in-the-plane resistance by conducting the electrical potential to the entire sub-surface of the coating at one time, much as with the transparent thin-film noble metal layer.

The thickness of the coating will depend on the material employed and the desiderata of the intended application. Thicker coatings have better conductivity but poorer light transmission properties, and vice versa. Generally, for transparent applications, the coating will be formed with a thickness in the range of 0.1 to 5 microns, and where transparency is not of great importance, such as in bio-reactors and associated applications, the coating may be of any convenient thickness.

The exact material/materials used for the coating/coatings will depend upon such parameters as transparency, resistivity, chemical stability, mechanical stability, biological inertness, cost, preferred methods of application, etc. However, preferred materials for forming the coating 2 are tin oxide ($SnO_2$) and indium oxide and various combinations of the two, (the ITO family) and various combinations of the two doped with other materials. Other materials suitable as transparent thin film conductors and which may be employed for forming the coating 2 or layer 2a include tin oxide doped with either fluorine or antimony and indium oxide doped cadmium oxide, cadmium stannate, zinc oxide, zinc cadmium sulfite, and titanium nitride (TiN). Materials currently showing promise for use as transparent electrodes and which may also be contemplated for forming the coating 2 or layer 2a are: rubidium silver iodide ($RbAg_4I_5$), dieuropium trioxide, lanthanum hexaboride, rhenium trioxide, and divanadium pentaboride.

In addition to being non-cytotoxic and capable of supplying a surface suitable for cellular adhesion and growth, the coating material must also have the added properties of withstanding attack by acidic and basic organic solutions, nondegradation by autoclaving, and be relatively resistant to mechanical degradation, and resist if not withstand electro-chemical attack in application.

Although the mechanism is not yet fully understood, early observations appear to indicate that the pyrolytically deposited $SnO_2$ surfaces may give rise to mitogenesis enhancing properties over that of currently used surfaces. Whether this is due to the mechanical surface properties induced by pyrolytic deposition, a chemical effect of tin ions nearby, the conductive nature of the $SnO_2$ film, or a combination between these properties, is not at this .time discernable. It is felt that the surface properties (i.e. smoothness, etc.) along with the inert conductive nature are the essentially interactive components and that materials other than that of SnO₂ will show the same effect, although to differing extent. Other as yet unrecognized effects may also be found.

Figure 4:
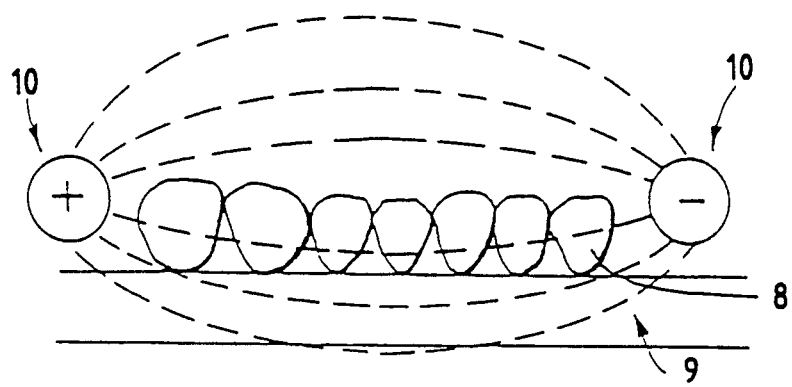
FIG. 4a shows diagrammatically a conventional substrate surface with charged cells adherent thereon.
FIG. 4b shows diagrammatically the shape of the electric force field emanating from a conventional charged plate electrode.
FIG. 4c shows the shape of the electric force field using a thin film conductor in accordance with an embodiment of the invention.
Figure 4A:
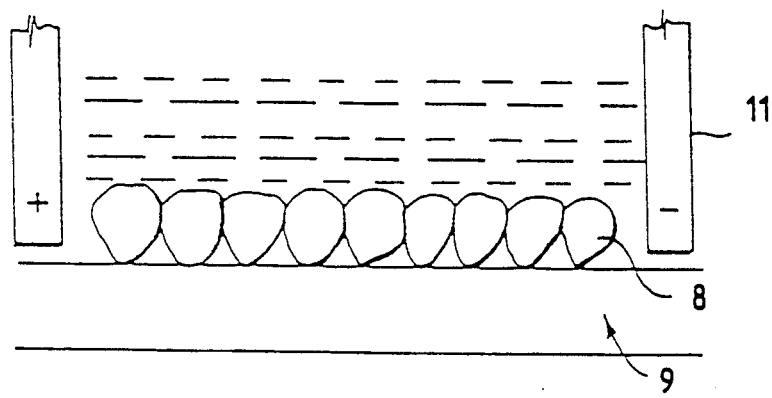
Figure 4B:
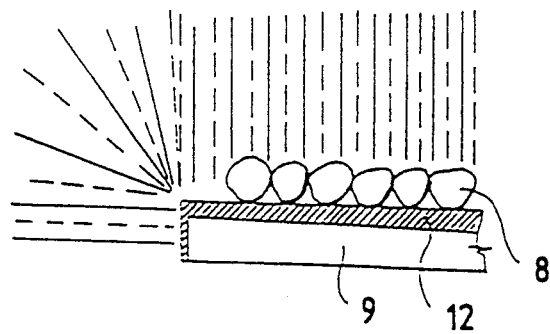

FIG. 4a shows diagrammatically the conventional method of subjecting adherent cells to an electric field. Cells 8 grow while attached to a substrate 9 and a circular electrode 10 is placed on either side of the cell. FIG. 4b shows the shape of the electric force field emanating from a charged plate electrode 11.

Lines of force are shown in short dashes and the proximity of lines to each other indicates the relative intensity of force. Lines of current flow are shown with longer dashed lines. It can be seen that the lines of force and of current flow are propagated in a side-to-side fashion, across the cells. This may lead to an electrical interaction between the cells, especially if the cell membranes are touching. The difficulty in establishing lines of force perpendicularly through the cells is overcome by the use of the thin transparent conductive coating of the invention.

FIG. 4c shows the configuration of lines of force and potential current flow from a thin film conductor 12 according to an embodiment of the invention. It can be been that the lines of force are perpendicular to the direction of cell spread, creating the highest equipotential point near to the upper surface of the cell. It will be apparent that this shape can be of definite use, for example, if the wanted to "charge sweep" the upper surface of the cell of proteins on the surface, or of those occurring in the outer membrane surface.

Figure 3:
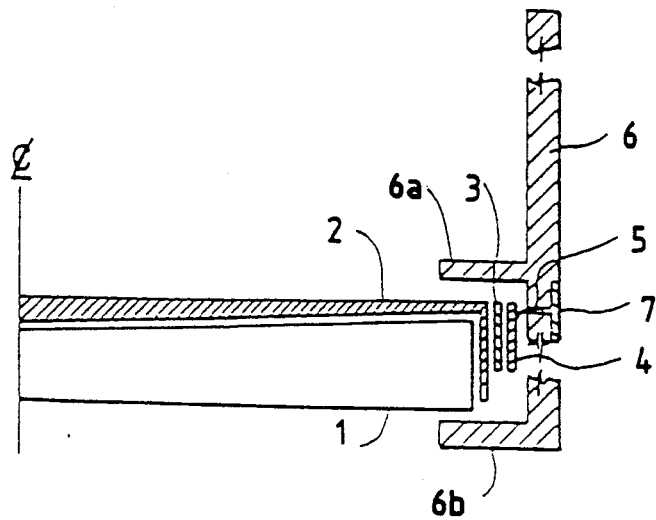
FIG. 3 is a partial cross-section of the dish shown in FIGS. 1 and 2, taken along line III—III of FIG. 2.
Figure 3A:
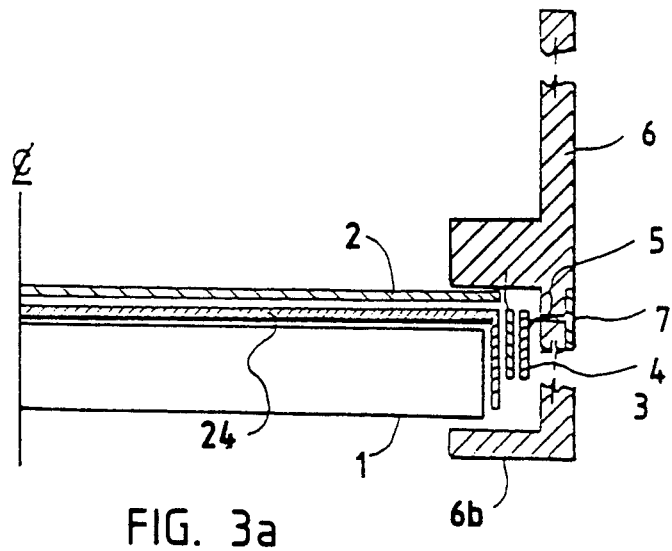
Figure 5:
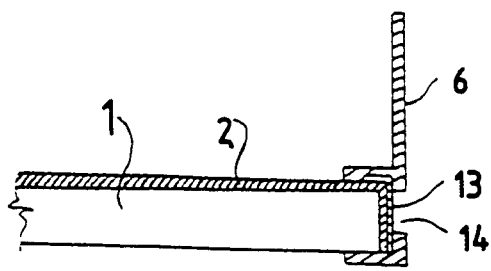
FIG. 5 is a partial cross-section of part of a electrode cell cultivation dish according to another embodiment of the invention.
Figure 5A:
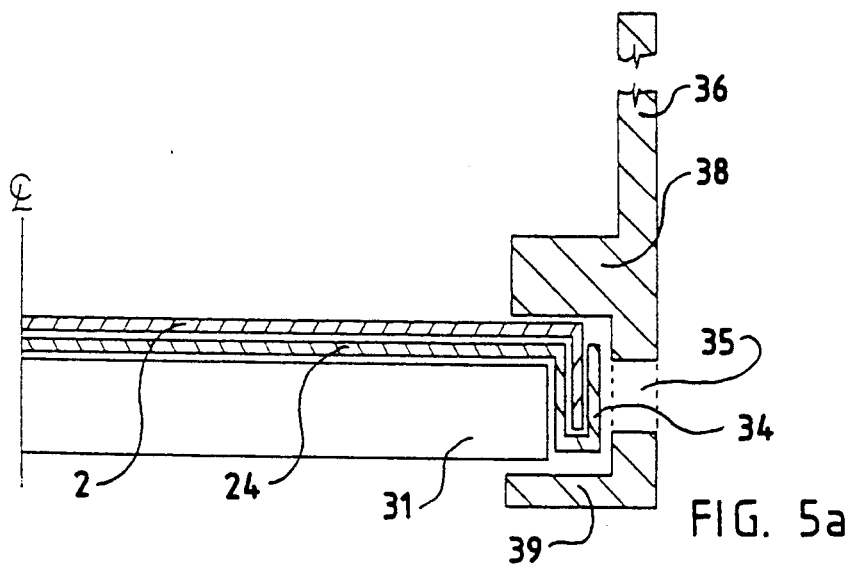
FIG. 5a is a partial cross-section of part of a planar electrode cell cultivation dish according to another embodiment of the invention.
Figure 5B:
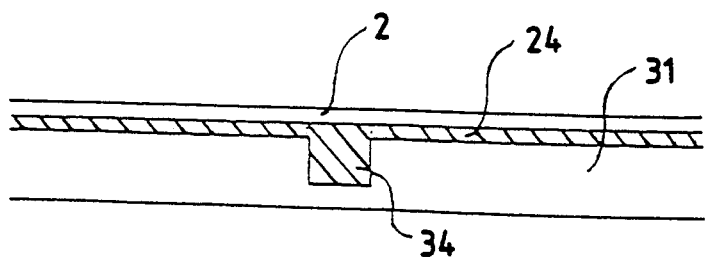

FIGS. 5, 5a, and 5b show other embodiments of the device of the invention which replace the metallic coating 3 and the distribution electrode 4, lead-in wire 5, and external electrical contact 7 of FIGS. 3 and 3a, with a deposition of a metal film 13, e.g. gold, silver, platinum, copper. Electrical contact is permitted by an aperture 14 in the side wall of the tubular enclosure 6, which allows contact with an external power electrode that passes through the opening FIG. 5 shows the metallic deposition electrode 13 formed in a ring encircling the vertical circumference and extending onto the upper surface of the coating 2. The ring electrode 13 may encircle only the vertical circumference.

Figure 5C:
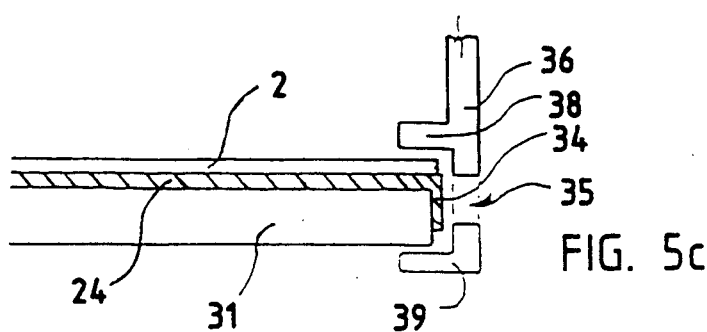
FIG. 5c is a partial cross-section of part of a electrode cell cultivation dish according to the embodiment of FIG. 5b.

FIG. 5a shows the radial distribution electrode 24 below the cell adhesion conducive coating 2 in an alternate embodiment of FIG. 2a. The radial distribution electrode may be deposited over the face of the substrate 1 and the vertical perimeter first, and the cell adhesion conducive coating a deposited afterwards, with a window to the metallic layer 24 being left open through the coating 2. Alternatively, only the upper surface of the radial distribution electrode need be coated with the cell adhesion conducive coating 2. FIGS. 5b and 5c show a further alternate embodiment where the metal film forming the radial distribution electrode 24, is deposited on the upper face of the substrate and has extending down the face of the vertical perimeter a strip forming a contact point 34 for externally applied power via aperture 35.

The substrate may also be frusto-conical in shape, i.e. the outer edge surface on which the film 13 is deposited may slope downwardly, outwardly, so that the upper edge of the substrate has a bevelled surface. This permits simplification of the process of depositing the metal film 13 which can then be accomplished in a single step. As may be appreciated, there are many ways and geometries available and conceivable in which to combine the coating, the distribution layer, the distribution electrode and the lead-in electrode.

FIGS. 8, 8a and 8b show a view from above of a style of receptacle for use with the pepetri dish of FIGS. 5 and 5a. The pepetri-dish 15 with an external power electrode aperture 16, slides over bevel-edged circumferential supports 22 held in place by a supporting body 21, whereupon a gold-plated spring electrode 17, connected to an electrical input jack 19 by a connecting wire 18, completes electrical contact with the indented electrode 13 (see FIGS. 5 and 5a) while a retaining spring 20 prevents the pepetri dish from slipping out of electrical contact. The dish 15 is provided with a cover 23.

The electrical jack 19 can be connected to an electrical ionizing source of preference, depending on the requirements of each experiment. It can be seen that the receptacle provides an efficient and convenient method for charging the pepetri-dish while allowing virtually total freedom for optimal examination of a culture in the dish. It is recognized that the shape of the retaining means and contact means may be varied in several ways, but have the basic element of the ability to supply an electrical connection to the pepetri dish, and many ways of doing this may be readily envisioned.

Given the current state of the arts in molecular manipulation of plastic-forming materials, it will be apparent that there exists the distinct possibility that coated substrate materials could be dispensed with in favour of conducting or transparent conducting plastic, conforming to the other constraints applied, such as adhesivity, non-toxicity, etc. While replacement of the conductive coating on a substrate with a plastic type material would remove the need for the coating, it still would represent the use of a conductive material for growing monolayer cells while treating them with applied electrical fields of a similar nature.

Using the pepetri as a starting point, a device for electroporation purposes may be fabricated wherein the cells are not subject to suspension insult and which presents a large area of cell membrane per cell, and wherein all cells may be presented equi-distantly from, and at an extremely close distances to a counter-electrode, which is preferably planar. In addition, in some cells the nuclear bulge will present a raised area of membrane as a portion of the upper membrane, depending upon the percentage of normal confluency of the culture, among other things.

Thus, an upper electrode made of the same (if desired) transparent, conducting, non-cyto-toxic material as the pepetri coating may be disposed opposite the pepetri dish with the monolayer of cells to be porated, with the conductive surface facing the upper surface of the lower pepetri-dish, and the material to be transfected suspended in an appropriate medium placed between the two planar electrodes and different electrical charges applied to each of the electrodes. Alternatively, the material to be transfected may be first electrostatically (or similar method) drawn onto a carrier surface which is then placed onto the upper (counter) electrode. The counter electrode and material carrier may then be disposed at a very close distance, such as 1 mm or less from the upper surface of the cells in the pepetri-dish, and appropriate electrical charges applied. The distance that the opposing electrodes may be placed relative to each other is an obvious advantage of the instant invention over any prior art, in this manner. Further targeting of the material to be transfected may be achieved by the use of appropriate electroporation media in which a large majority, if not all of the otherwise ionizable material is removed, leaving the material to be transfected as the only ionizable material. With this approach, material such as DNA and RNA and materials having only a very small charge may be made the current carrier, further increasing its up take into the cell.

It is recognized that this new geometry will simplify if not remove the current significant problem of determining at exactly what field intensity individual cell lines react to (for poration purposes and others), and the calculation of what field intensity a cell is actually being subjected to.

Figure 6:
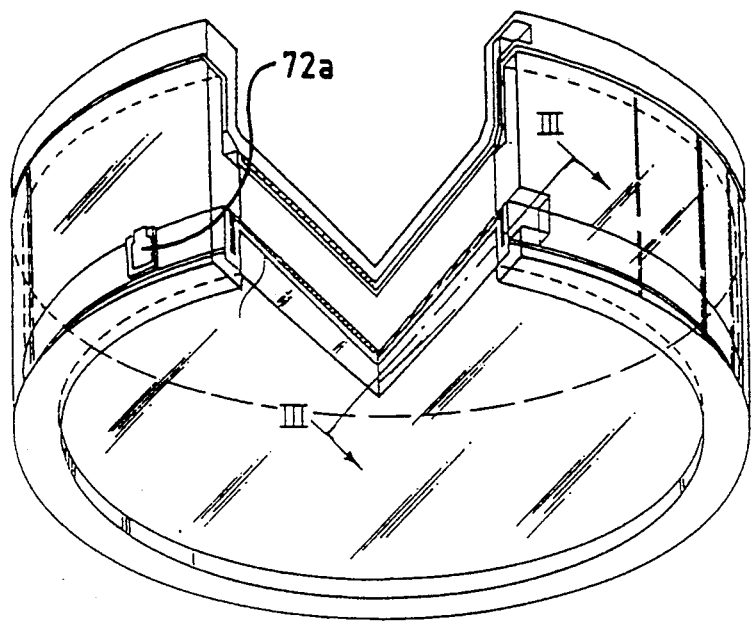
FIG. 6 is a cutaway isometric view of another embodiment of the invention showing the relationship between a counter electrode and a pepetri dish.
Figure 6A:
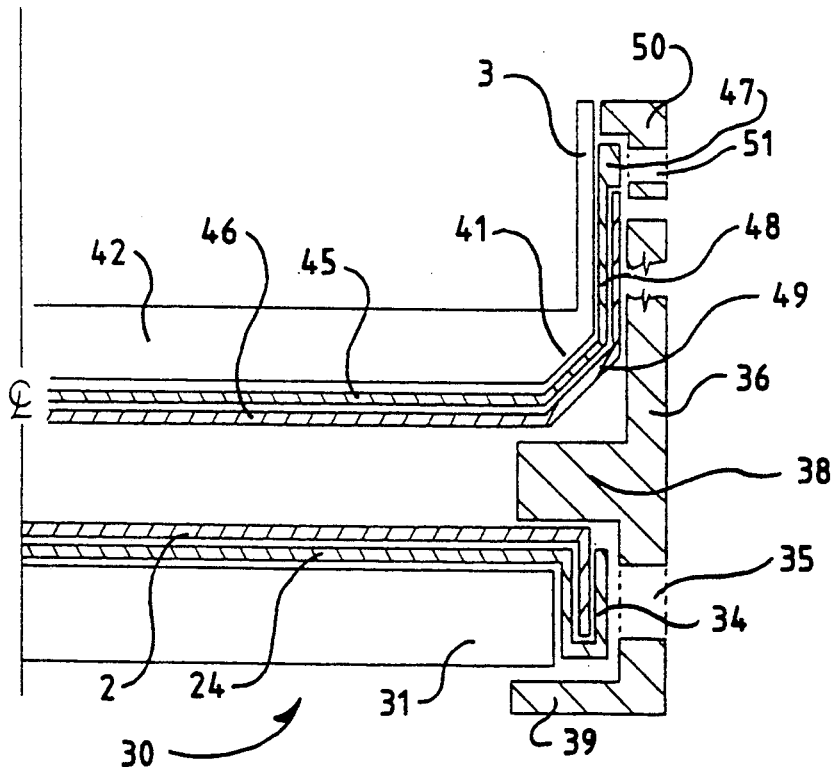
FIG. 6a is a partial cross-section of the embodiment shown in FIG. 6.

FIGS. 6 and 6a show an embodiment of the above device. The lower (cell growth) electrode 30 base material 31 may be plastic or glass and having disposed over the upper surface and down the outer circumference a thin-film layer of metal or semi-conductor material forming the radial distribution electrode (RDE) 32 and wherein the metal may either of the noble the when exposure to the electrolytic transfer media (ETM) or poration media PM is preferred, or of another metal when it is expected to be overlaid with the electrically conductive cell adhesion conducive coating (CACC) 33 or transparent CACC (TCACC) 33. The total coating thickness of the radial distribution electrode and cell adhesion conducive coating for transparent purposes such as optical viewing should not be so great as to substantially interfere with light passage. When non-view apparatuses are required, the coatings may be of any thickness, excepting those that would fall below minimum function parameters.

The radial distribution electrode 24 extending across the face of the disc and onto the disc edge, terminates in a built up layer of metal in the form of a square or rectangle that acts as an electrical contact 34 for the exterior power electrode 37 and aligns with an aperture 35 in the pepetri fluid retaining wall 36 allowing contact with the exterior power electrode 37. This type of contact arrangement is shown in FIGS. 3 and 5. Alternatively, the radial distribution electrode may extend substantially the total diameter and leave the face onto the edge as a strip which ends in an electrical contact point 34 as shown in FIGS. 5a, 5b and 5c.

Extending radially inward on both the lower and upper edge of the disc, are gripping flanges formed in such manner so as to provide a water and moisture proof bond with the disc. The inner flange 38, thicker than the outer flange 39, serves as the counter electrode support means and depth gage. The counter electrode support means 38 does not necessarily have to keep the counter electrode 40 and lower electrode 30 planar to each other, although this may be preferred. The vertical inner face and upper surface of the flange 38 may be made of, or coated in a material non-conducive to cell adhesion so as to prevent cell growth up the face and over the upper surface of the flange. Depending upon style of counter electrode used, the counter electrode support means 38 may also include around its inner diameter and upper surface, surface tension relief openings 41 to facilitate removal of the counter electrode 40. Surface tension relief openings 41 may be in the form of grooves or notches or similar and extend completely around either the outer edge of the counter electrode 40 or the inner edge of the counter electrode support means 38. These notches aid in breaking the surface tension of the fluid when the counter electrode is removed from the lower electrode.

The counter (upper) electrode 40 may be of the radial distribution type, having disposed upon it either a transparent or non-transparent cell adhesion conducive coating as the electrode. Alternatively, the counter electrode may be formed only of a thin-film of preferentially noble metal. In another alternative, the substrate and coating may be dispensed with and a solid metallic electrode used.

According to the first embodiment., the outer diameter of the substrate disc 42 forming the counter electrode 40 and the support the counter electrode support tube 43 is sufficiently less than the inner diameter of the upper fluid retaining walls 36 of the lower electrode 30 so as to allow the counter electrode 40 to be inserted into the pepetri dish and allow the counter electrode surface tension relief openings 41 to rest on the upper face of the counter electrode support means 38. The radial distribution electrode 45 film if employed, is of a diameter approximately equal to the inner circumference of the counter electrode support means 38 while the coating of electrically conductive cell adhesion conducive coating 46 disposed on it has a nominally larger diameter than the radial distribution electrode 45 or inner diameter of the counter electrode support means 38 so as to prevent direct contact of radial distribution electrode with the electroporation media. The radial distribution electrode 45 film extends out from under the cell adhesion conducive coating 46 at one point, over the edge of the base material 42 and continues up the outside of the counter electrode support tube 43 in the form of a strip 48 which terminates in an electrical contact point 47. The radial distribution electrode connecting strip 48 is insulated by means of insulating strip 49 formed of a thin film strip coating of $SiO_2$ or equivalent material, which terminates next to the electrical contact point 47, so that electrical contact with the radial distribution electrode 45 occurs in an insulated fashion from contact with the electroporation media, which may by displacement extend up the annular opening between the counter electrode support tube 43 and the pepetri fluid retaining wall 36.

Mounted externally at the top of the counter electrode support tube 43 is the counter electrode support tube flange 50 which is in L-shaped toroid with the base of the L inwardly and upwardly directed. The counter electrode support tube flange 50 is bonded onto the exterior of the counter electrode support tube 43 and nominally overlaps the insulating strip 49, and has provided an external power electrode aperture 51, situated over the electrical contact point 47, to receive the external power electrode 52.

The counter electrode support tube flange 50 and the top of the pepetri dish wall 36 may have interlocking registration marks so that when assembled the counter electrode external power electrode aperture 51 and the lower electrode external power electrode aperture 35 are vertically disposed from each other. These may take the form of a downward projecting V from the counter electrode flange and a complimentary V groove in the top of the pepetri dish wall 36.

The distance that the lower electrode 30 and counter electrode 40 are separated, along with other factors such as media composition, cell type, will determine the voltage requirements, and subsequently, the current requirements for poration to occur. In the preferred embodiment the electrodes are displaced 1 mm or less from each other, but need not be as close as this. Given potential process refinements they may be disposed within a few cell diameters of each other. In the preferred embodiment, the voltage will be 25 volts or less to create sufficient potential for poration.

Thus, the instant invention permits a method of subjecting in situ adherent cells to electrical fields of sufficient intensity to induce electroporation of in situ adherent cells while said cells are adhered to an electrode surface, which comprises the steps of cultivating adherent cells in a culture media on an electrically conductive surface which is characterized by affording an upper surface conducive to cell adhesion and growth; replacing said culture media with a liquid media appropriate for electroporation of cells; supporting a counter-electrode at a close distance from said surface having said cells adherent thereon so that said counter-electrode is in contact with said electroporation media; applying a source electric potential of sufficient intensity to effect electroporation to said surface and said counter electrode; removing said counter-electrode and replacing said electroporation media with said culture media. This represents a tremendous saving in labour, cost and in the risk of contamination over, and affords results hitherto unachievable by, the prior art.

With a readily controlled planar-projected electric field such as made possible by the instant invention a device with appropriate sensing means, such as thin-film electrodes disposed onto the cell adhesion conducive coating and isolated from the coating so as to be only in conductive contact with the media, and connected to an electrical field intensity measuring device appropriately interfaced to a micro-processor, that one has an "intelligent" electroporation device (i.e. a device capable of applying ever increasing electrical potential until the cells have porated, and capable of sensing at what field intensity the cells have porated), as well as a device for recording hitherto unavailable information concerning the poration potential required for various cell lines and the effects of various media compositions on the types and sizes of porations that may occur.

A yet further embodiment of the device allows the hitherto unachievable process of time-targeted S-phase introduction of exogenous material such as DNA, RNA, and proteins via electro-transfection into synchronized cell cultures which would allow researchers to determine the start time of a particular section of code replication, which is complex information to deduce because replication is a multi-point parallel process rather than a serial process. To allow the material introduced into the cell to be incorporated into the DNA of the target cell for a permanent expression, it is advantageous to know when the target site will replicate. Incorporation prior to replication obtains the greatest probability that the daughter cells will permanently express the new code, whereas incorporation after target site replication may result in only a transient expression. Since the applied voltages are very small, and no insult incurred by the cells, a large percentage of cells survive the electroporation.

The device assists in the mapping process by allowing time correlated introduction of exogenous material into synchronized cells. Since virtually no cell death occurs, and cells do not leave the S-phase, extremely high expression frequencies become possible. By using time correlation and serum stimulated synchronized cells, resulting expression efficiencies of integrated material may be directly or not transfection occurred prior to a given site's replication period. By using batch transfection of several different markers simultaneously, and stepping through the S-phase in discrete timed steps in a succession of related experiments, information as to what sites are undergoing replication at what time becomes available. Some of the markers making up a given batch may prevent or enhance the expression of other markers in the given batch. Since cell populations remain essentially intact and no base population shift occurs, very high experiment-to-experiment correlations can be made, further increasing the available data. The entire procedure may be effected and recorded by microprocessor means, and is down-loadable to a system processor for recordal purposes by means of appropriate software.

Very high rates of expression should be obtainable, barring loses due to replication correction undertaken by the cell. Information received as a result can be used to build a map of replication sites in relation to time and thusly be used to determine the replication sequence for a given DNA strand.

A further embodiment allows a plurality of precisely timed electroporations of synchronized cultures to be effected sequentially by a microprocessor and appropriate software operating as a control unit. Since there is very little if any shift in the base population of the synchronized cells, the experiments will have a high degree of correlation with each other, further increasing the amount of information that may be deduced. The control unit may have provided a program to correlate the marker, the time into S-phase of introduction and resulting expression or non-expression into a map of the sites undergoing replication at any given time in the S-phase.

Thus, the instant invention may be used in a method of mapping DNA replication sequences by time-correlated in situ electroporetic introduction of exogenous material into synchronized adherent cell cultures on an electrode surface while said cells are in their S-phase, which comprises the steps of: preparing, culturing and serum stimulating adherent cells cultures in one or more lower units of devices for subjecting adherent in situ cell cultures to an electrical field while said cells are adherent to an electrode surface, said one or more lower electrode units comprised of an electrically conductive coating characterized by affording an upper surface conductive to cell adhesion and growth, and having a sensing electrode disposed on an insulating layer disposed on said coating and electrode means in contact with said coating, inputting serum-stimulation time and start of S-phase into control unit, said control unit comprising means to detect electroporation fluid ionization, means to discriminate the transmembrane flow of ions from said cells into said electroporation fluid when said cells porate and generate a corresponding modulating signal, means for said modulating signal to control source of external electrical potential, and software to control the procedure; preparing an electroporation media, said electroporation media consisting of a solution osmotically balanced for cell survival and ionizable components and having in suspension one or more types of code, proteins or other materials desired to be entered into the cells, replacing culture media with said electroporation media, inserting into each of said one or more lower units of said device, upper upper units comprising counter-electrodes at a close distance from said coating having said cells adherent thereon, wherein said counter electrodes have a sensing electrode disposed on an insulating layer disposed on their surface and electrode means in contact with said counter-electrode; ensuring said electroporation fluid is in contact with said cells, said coating, said counter-electrode, and said sensing electrodes in each of said devices; connecting the sensing electrodes of each of the one or more devices to means for detecting poration of said cells in said one or more devices; connecting said lower electrode unit and said counter-electrode unit of each of said one or more devices to their respective external electrical terminals; inputting into the control unit the electroporation sequence for each of one or more said devices, the delay period into S-phase of the first poration, and the delay period between each subsequent poration; enabling the control unit; replacing the electroporation fluid with culture media; correlating the expression vs non-expression results and inputting resulting data along with the type of code, protein or other material into the control unit data-mapping program. The device may also give an indication when the process has been completed.

Figure 7:
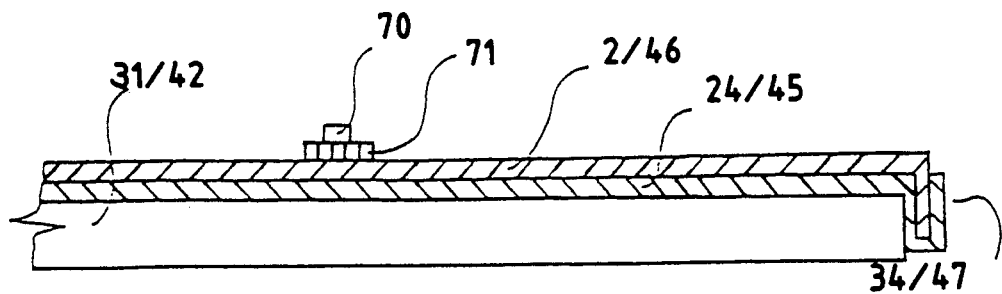
FIG. 7 shows a cross-section through an electrode surface of the invention and showing an ionization sensing electrode.
Figure 7A:
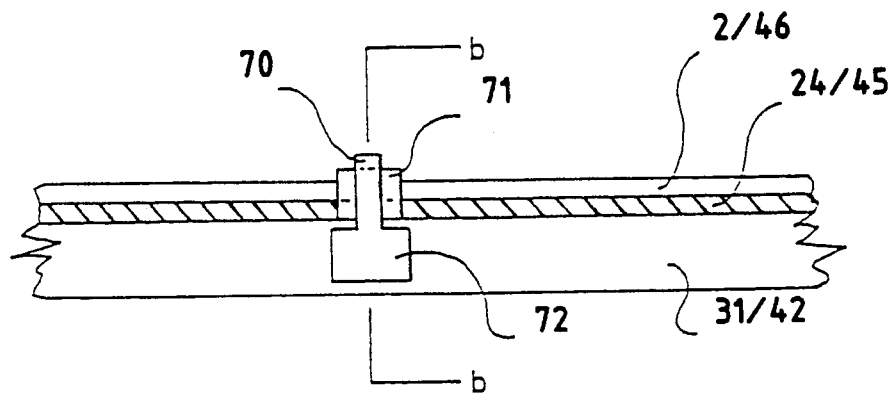
FIG. 7a shows a cross-section through an ionization sensing electrical contact point, according to one embodiment of the invention.
Figure 7B:
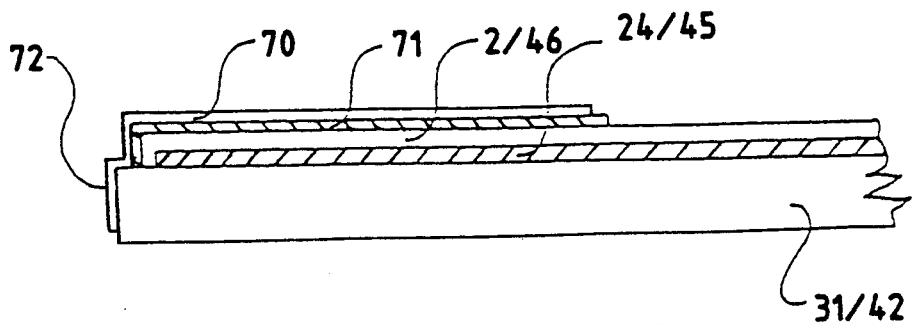
FIG. 7b shows a partial section of FIG. 6 with the ionization sensing electrode aperture in its relative position.

Referring now to FIGS. 7, 7a and 7b, ionization potential sensing means 70 may be placed on the lower electrode 30 and counter electrode 40 by laying down on the T/CACC 2 or 46 coated radial distribution electrodes 24 or 45, an insulating thin film strip 71 of $SiO_2$ or similar material, extending from a contact source on the upper-outer face of the substrate 31 or 42 and over the outer circumference and thence outward onto the electrode field area of the lower or counter electrode surface 2 or 46 in the form of a strip. Over laying this strip 71 of insulating material is the sensing electrode 70 formed of thin film deposition noble metal or other material. The ionization potential electrode 70 extends in a thin strip centered on the insulating thin film strip 71 and is of a width narrower than the strip 71 so as to preclude contact with the T/CACC 2 or 46, and terminating in a rectangular or other shaped external sensing electrode contact area 72.

Shown in FIG. 6 is the lower electrode sensing means contact 72a. and not shown is counter electrode sensing means contact 72b. In the case of the counter electrode, the ionization sensing electrode strip 70 extends over the outer circumference and up the face of the counter electrode support tube 43, and terminates in a rectangular or other shaped external sensing electrode contact area 72b (not shown). Apertures are provided for the external sensing electrodes for access the contact areas 72a and 72b in the same fashion as for the external power electrodes discussed earlier.

The sensing electrode contact means and the power electrode contact means may be radially displaced from each other'such as 90 degrees apart, so that no errors, such as attempting to sense from the power electrode (coating 2 or 46), or applying external power to the sensing electrodes can occur.

When the externally applied electric field climbs in intensity, electroporetic disassociation of the electroporation media takes place as motile ions are drawn to their corresponding electrodes and an electrical charge will be stored as an electrophoretically imbalanced solution. The ionization sensing electrodes, coupled to a high impedance circuit as part of a tuned tank, or other circuit capable of being used for this purpose, serve to detect the extent of electrophoretic disassociation of the solution at any given instant. As the current carriers native to the electroporation media drift to their respective electrodes, the conductivity of the solution decays (resistance increases) resulting in the drifting of the tuned circuit from a given starting frequency. This measurement corresponds to the electroporation media disassociation only, until such time as poration of the cell membrane occurs. The cell membranes prevent the ionizable components of the cytoplasm from drifting externally to the membrane until such time as poration occurs. At such time, a momentary surge of non-native current carriers becomes available to the electroporation media. This momentary surge causes a momentary rapid shift in the electrophoretic disassociation curve of the causing a momentary deflection in the frequency of the tuned circuit and is converted into a control signal that is used to control the external power source to the lower and counter electrodes.

Figure 10:
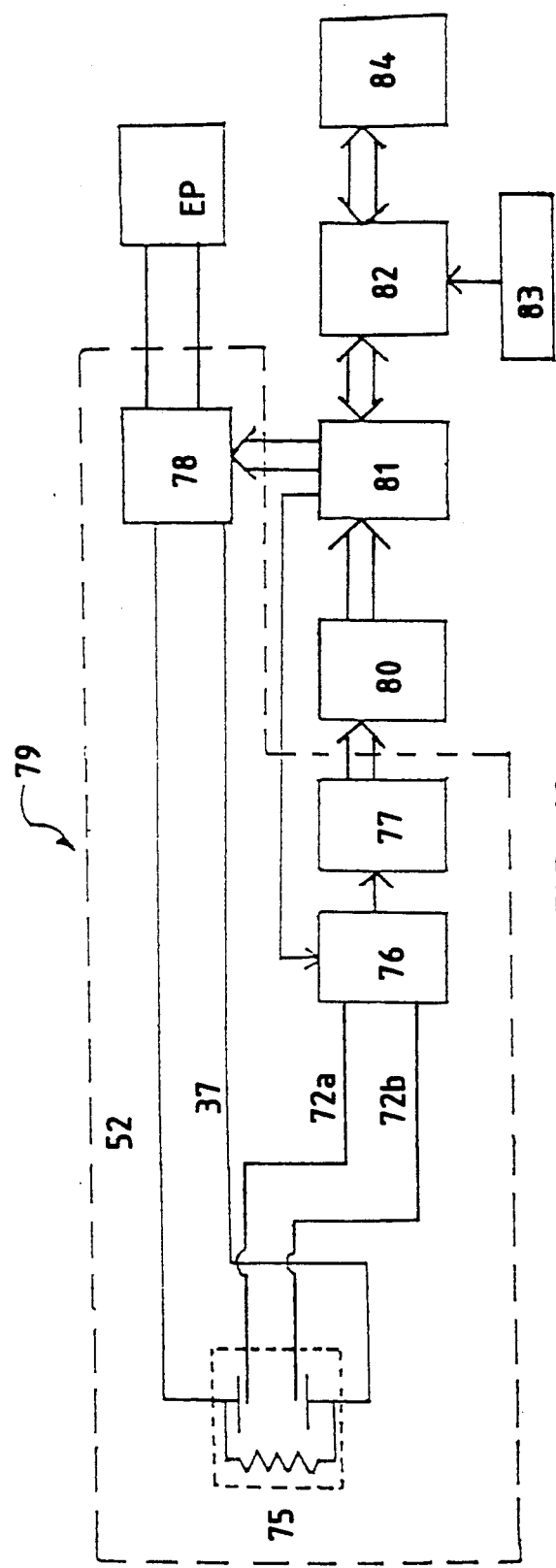
FIG. 10 is a schematic diagram of a circuit according to one embodiment of the invention.

Referring now to FIG. 10, the ionization sensing electrodes 72a and 72b placed so as to be vertically disposed from each other and in electrical contact by means of the electropolation media 75 (represented here as a variable resistor in series with a leaky capacitor), when coupled with an electrically isolated high impedance detector means 76 may be used to determine the degree of polarization of the electroporation media caused by the electric strain. Detector means 76 may be comprised of a differential amplifier circuit or tuned tank circuit. In an alternative embodiment, detector means 76 may comprise a conductivity meter.

The instant invention may be used in a method of detecting electroporation of in situ adherent cells while said cells are adherent to an electrode surface, which comprises the steps of cultivating adherent cells in culture med on an electrically conductive surface characterized by affording an upper surface conducive to cell adhesion and growth and having a first or second sensing electrode disposed on an insulating means disposed on said surface; replacing said culturing media with a media appropriate for electroporation; disposing a counter-electrode, having a first or second sensing electrode disposed on an insulating means disposed on said counter-electrode, at a close distance from said surface having said cells adherent thereon so that said electroporation media is in contact with said cells, said surface, said counter-electrode, and said first and second sensing electrodes, said electroporation media characterized by being in osmotic balance with said cells and containing motile ions; connecting said sensing electrodes to means for detecting polarization of said media upon the application of an electrical potential to said surface and said counter-electrode; connecting means for discriminating the transmembrane flow of ions from said cells when said cells porate to said polarization detection means, connecting said surface and said counter electrode to a source of electrical potential; applying an electrical potential to said surface and sad counter-electrode to porate said cells; recording said detection of said poration of said cells; removing said counter-electrode and replacing said electroporation media with said culturing media.

The output signal from the detector stage 76 may be converted from an analog signal to digital via A/D 77. Connected to the lower and counter electrodes of the electroporation chamber is a source of external electrical power EP controlled by switch 78 which may be transistorized. These units may form the basis of an electroporation module 79.

Several electroporation modules 79 may be connected to a versatile interface adapter 80 which would allow microprocessor 81 to have fast access to the output of each module to the hardware addressing approach which is significantly faster than other techniques. Microprocessor 81 may be used to calibrate or set the detector circuit 76 operational parameters. The microprocessor may also control via output signals a bank of addressable switches (not shown), with the electrical power being delivered individually to each electroporation module 79. With this arrangement, switch 78 would be replaced by an equivalent unit in the above mentioned bank of switches.

The microprocessor program 82 may be controlled either by operator keyboard 83 input, or external microprocessor 84, or by a combination of both. Additionally, the program 82 may retrieve and store information concerning the conductivity, field intensity at time of poration, cell type, ti e into S-phase among, other data the operator may wish to have available. Several electroporation modules 79 may be linked to the microprocessor/s, providing very accurate time control over a large number of related porations.

The use, design and applications of microprocessors for gathering information and process controlling is well known in the art of electronics, and it is beyond the scope of this specification to outline all feasible methods of designing such circuitry. To those skilled in the art of microprocessor applications, such criteria are a merely a matter of design. The same is true of the program required to conduct the process. The software is highly dependent on the hardware features. The process as outlined should provide a person skilled in the art of electronics and programming sufficient direction as to the features pertinent to the design of appropriate hardware and software.

The device would allow acurate analysis of media composition changes on time/ voltage/ integration frequency. The device may be programmed to calculate duty-cycle parameters in an automated process where different cell lines exposed in different media would be used primarily.

In this embodiment, the device may be used in a method of controlling an electrical field being used to induce poration of in situ adherent cells while said cells are adherent to an electrode surface, which comprises the steps of: culturing adherent cells in a culturing media on an electrode surface forming part of a means for subjecting adherent cells to an electrical field wherein said means for subtracting adherent cells to an electrical field also has means for detecting the electrically induced ionization of an electroporation media; connecting means for discriminating a transmembrane flow of ions from said cells when said cells porate to said means for detecting the electrically induced ionization of an electroporation media forming part of said means for subjecting adherent cells to an electrical field; connecting means for converting said discriminated transmembrane flow of ions into a modulating signal; replacing said culturing media with an electroporation media characterized by being in osmotic balance with said cells and containing motile ions; connecting means for applying said electrical field to means of subjecting said cells said electrical potential under control of said modulating signal; enabling said discriminating means to apply sad electrical potential to said device for subjecting said adherent cells to said electrical field; replacing said electroporation media with said culturing media.

In an alternative technique, instead of being placed in suspension in the electroporation media, the material to be transfected may be first electrostatically (or similar method) drawn onto a carrier surface which is placed onto the upper (counter) electrode. The carrier surface ma-y be of materials like PAG or similar filter and membrane materials. The counter electrode and material carrier may then be disposed at a very close distance, such as 1 mm or less from the upper surface of the cells in the pepetri-dish, and appropriate electrical charges applied. The distance that the opposing electrodes may be placed relative to each other is an obvious advantage of the instant invention over any prior art, in this manner. Further targeting of the material to be transfected may be achieved by the use of an appropriate electroporation media in which a large majority, if not all of the other ionizable material is removed, leaving the material to be transfected as the most ionizable material. With this approach, material such as DNA and RNA and materials having only a very small charge may be made the current carrier, further increasing its uptake into the cell. It is recognized that this new geometry will simplify if not remove the current significant problem of determining at exactly what field intensity individual cell lines react to (for poration purposes and others), and the calculation of what field intensity a cell is actually being subjected to and what effect media composition plays in the process.

A look-up table may be generated so that for a given cell type, and for a given exogenous material, requiring a given media, the apparatus would need only a program selection number relating to cell type, a media type, and a target molecule (extra-cytoplasmic material such as DNA, RNA, etc.) reference name or number, the device can set the optimum conditions for each poration, rather than having the experimenter having to continuously reset the intensity/time functions for change in cell line, cell type, media, specialized media commitments, etc as is the current practice. Since the device measures the conditions required to induce poration, and detects when poration occurs, substantial reductions in current mediated cell death will be realised since only enough energy to induce poration is introduced into the system.

Microprocessor controlled bursts of short duty-cycle ionization may be employed so as to intermittently drag the targeted molecule without incurring damage to the coating. In addition, the microprocessor may have control over a wave-form generator allowing electrical power of many varying waveforms to be applied.

By use of low ionization potential electrotransfection media, such as the earlier mentioned poration media, higher electrical field intensities may be used if desired. Removal of the not required ions such as Cl will reduce electrode damage at occurs at higher voltages and currents. Power levels sufficiently high enough to damage the T/CACC should not be required because of the distance of the opposed electrodes. Since electrically induced cell membrane perturbations are the basis of pores opening in the cell and research shows that this poration occurs virtually instantly when the trans-membrane potential passes the 0.7 to 1.1 V region, voltage fields of sufficient intensity to induce poration should be achievable in the 20 volt and less region. This is of course highly dependent in the CESM height and media being used. Some variance may be found due to the cell type, depth or thickness, targeted molecule (net charge, size, shape).

The above procedures may be advantageously effected by the chilling of the cell cultures prior to the application of electrical energy. This also holds true for chilling during the procedure. While the chilling is not required to prevent over-heating of the cells and poration media, studies have shown that the pores produced, begin to "heal" or close almost as soon as the pore inducing field is removed. Chilling the cells results in a somewhat greater time required for the membrane materials to flow back into their original position. The desirability of chilling, will however, need to be assessed for different applications.

FIG. 9 shows the relationship of an assembled lower and upper electrode forming an electroporation device and inserted into a handling device. The pepetri (lower electrode 30) and counter electrode 40 may be inserted into a handling device 89 used to both transport the electroporation apparatus and act as an electrical interface jack connecting the lower electrode 30 and counter electrode 40 and the external ionizing source leads 37 and 52 together. Lower electrode electrical contact 34 is made accessible to ionizing source electrode 37 via means of aperture 35. Counter electrode electrical contact 47 is made accessible to ionizing source electrode 52. Both contact electrodes 37a and 52a may be in the form of a spring, and when the electroporation device is inserted into the handling device 89, make conductive contact with their appropriate electrical contact. The arms of the handling device are separated at their outer ends by a distance nominally larger than the outside diameter of the pepetri, and then converge slightly to a distance somewhat less than the diameter of the pepetri. The longer arm of the two has disposed at its outer end, and directed inwardly, a retainment spring (element 20 of FIG. 8), which serves to lock the pepetri and counter electrode into the handling device and bring electrical contacts 37a and 52a into contact with electrical contacts 34 and 47. Electrical contacts for the sensing electrodes may be built in the same fashion as the power electrodes and match up with their appropriate apertures at the junction of the two arms of the handling device. Further, there may be provided in both arms at appropriate locations, compression springs 90 serving to keep the counter electrode 40 and lower electrode 30 in close contact. The handling device may be so designed so as to allow its use on optical microscope stages when it is of interest to visually inspect the cells and/or process for film recording.

Although the aspects of the present invention have been fully described by way of example with reference to the accompanying drawings, it should be noted that many of the embodiments disclosed may be interchanged in part or in total with other embodiments outlined, and as a result numerous variations in design become possible, and as such, these various changes, modifications and other embodiments will be apparent to those skilled in the art. Therefore, unless such changed and modifications otherwise depart from the scope of the present invention, they should be construed as being included herein.

It will be apparent that many further uses for the novel device of the invention will be readily obvious to those skilled in the theories and procedures of molecular cell microbiology, and especially to those skilled in the art of application of electric fields to cells, such as for use in electro-fusion.

To those skilled in the at of electrofusion of cells, it will be readily apparent that slight modifications to the device, such as the culturing of another monolayer of a different cell line on another modified pepetri surface, and bringing the two of them into contact such that the upper cell surface of one is in contact with the upper cell surface of the other and an electrical charge applied, offers a new and radically different way with which to subject substantial numbers of the cells to a condition to promote cell fusion and with which to be able to study optically the process of cell fusion. In this case the electrodes would serve to deliver either AC fields and/or DC fields.

It will also be apparent that the study of cells, and the study of micro-organisms such as bacteria and viruses not requiring to be adherent to a surface, will also benefit from the ability to expose them to a uniform electric field while under optically observable conditions, such as generated by the instant invention. Finally, to those skilled in the art of cell culture, it will be apparent that the new geometry and other features of the instant invention also have application in the field of bio-reactors and associated devices and that electrically conductive coatings conducive to cell adhesion and growth have direct and wide spread potential applications in the field of bio-sensors and bio-sensory apparatuses.

It will also be apparent that the culture surface may be fabricated in the form of a checkerboard, in which, using current ion beam etching and similar techniques such as used in the fabrication of very large scale integrated circuits, that individual "checkerboard squares" may be fabricated of alternate areas of conductive and non-conductive material wherein each conductive square may be individually addressable, such as by current computer means, and have one or more nerve cells or brain cells attached thereto and addressed thereby, and will have application in such areas as nerve cell growth and communication studies, bio-sensors, bio-implants and similar.

A further modification of the instant invention contemplates the disposition of an electrically insulating layer of, for instance $SiO_2$ type materials onto the upper surface of a pepetri dish (the coating 2 now becomes optional), a similar disposition of $SiO_2$ type material (those materials applicable to thin-film techniques and that have the required properties to be conducive to cell adhesion and growth) onto an opposing counter-electrode wherein a radial distribution electrode is formed on the substrate, and the application of electrical potentials to the opposing electrodes so that the cells cultured on the lower (or upper) $SiO_2$ surface are subject to intense electrostatic fields, (becoming unit di-polar capacitors in an ionizable solution comprising one half of two capacitors) sufficient to induce poration of the cell membrane. A further alternate embodiment of this device is the automation of the device by using thin-film electrode strips disposed onto the $SiO_2$ coatings, serving as media ionization sensing electrodes so as to be able to sense the permeabilization of the cells by means of sensing the outrush of ions from with-in the cell membrane. The momentary current pulse occurring, although small, can serve as means to sense the poration of the cells, (earlier alternate embodiment) and under appropriate micro-processor control, electro-static fields can be applied and controlled until such time as poration occurs, and all significant data recorded. Devices of the nature above can serve to automate the process of electroporation so that prior experimentation to determine the required electrical potential needed for poration of a given cell line may be dispensed with. Further, the device will provide measurable information as to the effect of media composition on required field intensities for electroporation when current is not applied.

The method of use is almost identical of that to the above disclosed devices, with the exception that the electroporation fluid would require a somewhat higher number of motile ions and the electrical potential required to induce poration may be substantially higher and for a longer period of time.

The foregoing material serves to demonstrate the tremendous untapped potential of the novel instant invention for use in the fields of microbiology, cell microbiology, genetic engineering bio-reactors and bio-sensory apparatuses.

Those skilled in the art of microbiology or electronics will see that many various combinations and embodiments may be foreseen using the nature of the adhesion conducive properties of some semi-electrode materials, and as such, this disclosure should be construed as referring to these alternatives as well.

What is claimed is:

1. Apparatus for the transfection of exogenous material into in situ adherent cells by means of electroporation while said cells are adherent to an electrode surface, said apparatus comprising:
    a chamber means wherein in situ adherent cells may be subjected to an electrical field or sufficient intensity to cause poration of cells while the cells are adherent to an electrode surface; said chamber means characterized by having at least one internal surface being an electrically conductive surface conductive to cell adhesion and growth forming a first electrode having a first surface a second internal face formed of an electrical conductor forming a second or counter electrode; and means for supporting said counter electrode in close proximity to said surface having cells adherent thereon;
    fluid retaining means for maintaining cells submerged in an appropriate medium while adherent to said surface;
    means for applying an electric potential or electrical ionizing source to said first surface and said counter electrode;
    means for detecting the poration of cells and converting said detected poration into a modulating signal;
    means for retaining a fluid in contact with cells, said first surface, said counter-electrode, and said sensing means; and
    means for controlling by said modulating signal, said electrical potential or electrical ionizing source.

2. Apparatus according to claim 1, wherein said means for controlling an electrical field being used to induce poration of in situ adherent cells, comprises:
    means for detecting a transmembrane flow of ions when cells porate;
    means for converting said detected transmembrane flow of ions into a modulating signal; and
    means for applying an increasing electrical potential to said chamber means;
    means for applying said increasing electrical potential under control of said modulating signal to said chamber means.

3. Apparatus according to claim 2, wherein said means for detecting the poration of cells, comprises:
    first and second sensing electrodes disposed on but insulated from said first surface and said counter-electrode;
    means for insulating said first or second sensing electrode from direct physical contact with said first surface or said counter electrode;
    means for retaining a fluid in contact with the cells, said first surface, said counter-electrode, and said first and second sensing electrodes;
    means connected to said sensing electrodes for detecting polarization of the fluid upon the application of an electrical potential to said first surface and said counter-electrode;
    means connected to said polarization detection means for discriminating the transmembrane flow or ions from the cells when they porate; and
    means for applying an electrical potential to said surface and said counter-electrode.

4. Apparatus as claimed in claim 1, wherein the electrically conductive surface affording a surface conductive to cell adhesion and growth is comprised of a conductive coating of a semi-conductor material.

5. Apparatus as claimed in claim 4, wherein the semiconductor material is selected from the group consisting of tin oxide, indium oxide and mixture thereof.

6. Apparatus as claimed in claim 4, wherein the conductive coating is selected from the group consisting of stannic oxide doped with fluorine or antimony, indium oxide doped with cadmium oxide, cadmium stannate, zinc oxide, zinc cadmium sulfite and titaneium nitride.

7. Apparatus as claimed in claim 4, wherein the conductive coating is selected from the group consisting of rubidium silver iodide, dieuropium trioxide, lanthanium hexaboride, rhenium trioxide and divanadium pentaboride.

8. Apparatus as claimed in claim 1, wherein the electrically conductive surface is deposited on at least one layer of material more electrically conductive than said electrically conductive surface.

9. Apparatus as claimed in claim 8, wherein the electrically conductive surface and said layer are transparent to an extent sufficient to permit optical observation of cells adherent thereon.

10. Apparatus according to claim 8, wherein said layer is selected from the group consisting of metals and semiconductors.

11. Apparatus as claimed in claim 2, wherein said polarization detecting means is selected from the group consisting or differential amplifier, tunable tank circuit and conductivity meter.

12. Apparatus as claimed in claim 1, wherein the electrically conductive surface affording a surface conductive to cell adhesion and growth is comprised of conductive plastic.

13. Method of transfecting exogenous material into in situ adherent cells by means of electroporation while said cells are adherent to an electrode surface, which method comprises the steps of:
    cultivating cells on an electrode surface conductive to cell adhesion and growth which forms part of a device for subjecting adherent cells to an electrical field, wherein said device for subjecting adherent cells to an electrical field also has means provided for detecting he electrically induced polarization of an electroporation medium;
    replacing the culturing medium with an electroporation medium having in suspension exogenous material desired to be entered into the cells;
    applying an increasing electrical potential to said device under control of a modulating signal;
    detecting the electrically induced polarization of the electro-poration medium used in said device;
    discriminating a transmembrane flow of ions from cells when the cells porate converting said discriminated transmembrane flow of ions into said modulating signal; and replacing the electroporation medium with culturing medium.

14. Method according to claim 13, further comprising a method of detecting electroporation of in situ adherent cells while said cells are adherent to an electrode surface, comprises the steps of:

cultivating adherent cells in culture medium on said electrically conductive surface conductive to cell adhesion and growth and having a first sensing electrode disposed on an insulating means disposed on said surface;

replacing said culturing medium with a medium appropriate for electroporation;

providing a counter-electrode, having a second sensing electrode disposed on an insulating means disposed on said counter-electrode, in close proximity to said surface having cells adherent thereon so that the electroporation medium is in contact with said cells, said surface, said counter-electrode, and said first and second sensing electrodes;

connecting said sensing electrodes to means for detecting polarization of the medium upon the application of an electrical potential to said surface and said counter-electrode;

connecting means for discriminating the transmembrane flow of ions from cells when the cells porate to said polarization detection means;

connecting said surface and said counter electrode to a source of electrical potential;

applying an increasing electrical potential to said surface and said counter-electrode to porate the cells;

recording said detection of said poration of the cells;

removing said counter-electrode and replacing the electroporation medium with culturing medium.

15. Method according to claim 13, further comprising providing at least two exogenous material in suspension wherein one of said exogenous materials effects the expression of the other of said exogenous materials when integrated.

16. Method according to claim 13, wherein the applied electrical potential can be as high as 25 volts.

17. Method according to claim 13, wherein said electrical potential is applied to a synchronised cell culture during an S-phase of said culture's life cycle.

18. Method according to claim 13, wherein said cells are cultured in synchrony.

19. Method pursuant to claim 13, wherein the cells are chilled prior to being subjected to electrical fields inducing electroporation.

20. Method according to claim 13, wherein said electroporation medium comprises low ionization-potential materials.

21. Method according to claim 13, wherein said exogenous materials are disposed on a carrier which is then disposed on onto said counter-electrode.

22. Method according to claim 21, wherein the electroporation medium low ionization-potential medium.

* * * * *